United States Patent
Diller et al.

(10) Patent No.: US 7,071,331 B2
(45) Date of Patent: Jul. 4, 2006

(54) SYNTHESIS OF QUETIAPINE AND PHARMACEUTICALLY ACCEPTABLE SALTS THEREOF

(75) Inventors: Dov Diller, Jerusalem (IL); Ben-Zion Dolitzky, Petach Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/785,244

(22) Filed: Feb. 23, 2004

(65) Prior Publication Data

US 2004/0220400 A1    Nov. 4, 2004

Related U.S. Application Data

(60) Provisional application No. 60/448,934, filed on Feb. 22, 2003.

(51) Int. Cl.
*C07D 281/02* (2006.01)
(52) U.S. Cl. .................................. 540/551
(58) Field of Classification Search ............... 540/551
See application file for complete search history.

(56) References Cited

U.S. PATENT DOCUMENTS 4,879,288 A    11/1989  Warawa et al. ............ 514/211

FOREIGN PATENT DOCUMENTS

| EP | 0 240 228 A | 10/1987 |
|---|---|---|
| EP | 0 282 236 A | 9/1988 |
| WO | WO 99/06381 A | 2/1999 |
| WO | WO 01/55125 A | 8/2001 |
| WO | WO 03/080065 A | 10/2003 |

OTHER PUBLICATIONS

Merck Index, 13th Edition, 8130 (2001).
Warawa E. J. et al., "Behavioral approach to nondyskinetic dopamine antagonists: Identification of Seroquel" *J. Med. Chem*. 2001, 44,372-389.

*Primary Examiner*—Brenda Coleman
(74) *Attorney, Agent, or Firm*—Kenyon & Kenyon LLP

(57) ABSTRACT

Provided is a novel synthesis of quetiapine employing phase transfer catalyst.

34 Claims, No Drawings

SYNTHESIS OF QUETIAPINE AND PHARMACEUTICALLY ACCEPTABLE SALTS THEREOF

RELATED APPLICATIONS

The present application claims the benefit of the Feb. 22, 2003 filing date of U.S. Provisional Patent Application 60/448,934.

FIELD OF THE INVENTION

The present invention relates to synthesis of quetiapine and pharmaceutically acceptable salts thereof.

BACKGROUND OF THE INVENTION

The structure of quetiapine, 2-(2-(4-dibenzo[b,f]-[1,4]thiazepin-11-yl-1-piperazinyl)ethoxy)ethanol, is shown below (I).

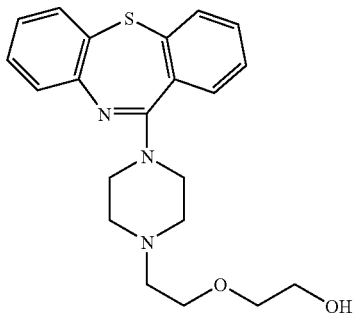

Quetiapine is a psychoactive organic compound that is an antagonist for multiple neurotransmitter receptors in the brain. Merck Index, 13th Ed., 8130 (2001). Quetiapine is an antipsychotic agent useful for treating, among other things, schizophrenia. Quetiapine can be made, for example, as taught in U.S. Pat. No. 4,879,288, incorporated in its entirety herein by reference.

As taught in the '288 patent, quetiapine can be made via reaction of 11-piperazinyl dibenzo[b,f]-[1,4]thiazepine hydrochloride and 2-(2-chloroethoxy)ethanol in a solvent. Reaction times are long (e.g. 24 hours). Also, starting materials such as the 11-piperazinyl dibenzo[b,f]-[1,4]thiazepine are undesired in the product and can be difficult to remove from the product.

There is a need for an improved process for making quetiapine from 11-piperazinyl dibenzo[b,f]-[1,4]thiazepine allowing shorter reaction times and affording a quetiapine product that contains a lower level of impurities (such as the unreacted starting material).

SUMMARY OF THE INVENTION

In one aspect, the present method relates to a process for making quetiapine comprising the step of reacting 11-piperazinyl dibenzo[b,f]-[1,4]thiazepine hydrochloride and 2-(2-chloroethoxy)ethanol in a solvent, especially n-butanol, toluene, or dimethyl formamide, in the presence of a base, especially sodium carbonate, a phase transfer catalyst, especially tetrabutylammonium bromide, and, optionally, an alkali metal halide, especially sodium iodide.

In yet another aspect, the present invention relates to a process for making quetiapine hemifumarate including the steps of: reacting 11-piperazinyl dibenzo[b,f]-[1,4]thiazepine hydrochloride and 2-(2-chloroethoxy)ethanol in a solvent, especially n-butanol, toluene, or dimethyl formamide, in the presence of a base, especially sodium carbonate, a phase transfer catalyst, especially tetrabutyammonium bromide, and, optionally, an alkali metal halide, especially sodium iodide, whereby a first slurry is obtained; separating the solid from the first slurry, whereby a liquid filtrate is obtained; combining the liquid filtrate with fumaric acid, whereby a second slurry is obtained; and isolating quetiapine hemifumarate from the second slurry. In this aspect, the present invention also relates to recrystallizion of the quetiapine hemifumarate so obtained from a solvent that is a lower alkanol, especially ethanol, or a mixture of water and a dipolar aprotic solvent, especially ethanol.

DETAILED DESCRIPTION OF THE INVENTION

The present invention provides a process of making quetiapine —11-[4-[2-(2-hydroxyethoxy)ethyl]-1-piperazinyl]dibenzo[b,f]-[1,4]thiazepine—with lower amounts of difficult-to-remove residual 11-piperazinyl dibenzo[b,f]-[1,4]thiazepine than hitherto realizable with the methods of the prior art. The process of the present invention is readily adapted to encompass the preparation of pharmaceutically acceptable salts of quetiapine, especially quetiapine hemifumarate.

As used herein, slurry refers to undissolved particles in a liquid.

The process of the present invention includes the step of reacting, in a suitable vessel, preferably with agitation (e.g. stirring), 11-piperazinyl dibenzo[b,f]-[1,4]thiazepine with 2-(2-chloroethoxy)ethanol in a solvent in the presence of a base, a phase transfer catalyst, and, optionally, an alkali metal halide. The reacting is preferably at a temperature greater than about 100° C., especially at reflux. The skilled artisan understands that reference to 11-piperazinyl dibenzo[b,f]-[1,4]thiazepine hydrochloride refers to the well-know dihydrochloride referred as such to in the prior art.

Phase transfer catalysts are an important aspect of the present invention and are well known to one skilled in the art of organic synthesis. Phase transfer catalysts are of particular utility when at least first and second compounds to be reacted with each other have such different solubility characteristics that there is no practical common solvent for them and, accordingly, combining a solvent for one of them with a solvent for the other of them results in a two-phase system. The phase transfer catalysts useful in the practice of the present invention are of the same type and used in the same manner and amounts as the phase transfer catalysts well known in the art. Examples of phase transfer catalysts useful in the practice opf the present invention include tetrabutylammonium bromide, triethylbenzylammonium chloride, and tricaprylmethylammonium chloride (Aliquot® 336) Tetrabutylammonium bromide is a preferred phase transfer catalyst in the practice of the method of the present invention.

The solvents useful in the practice of the present invention include the lower alkanols, aromatic hydrocarbons, and the so-called dipolar aprotic solvents. Preferably, the solvent has a boiling point at normal atmospheric pressure of about 100° C. or higher.

Lower alkanols are linear or branched aliphatic alcohols of general formula $C_nH_{2n+1}OH$, where n is 1 to about 6.

Normal butanol (n=4) is a particularly preferred lower alkanol for use in the practice of the present invention in certain of its embodiments.

Aromatic hydrocarbons useful as solvents in this and other embodiments of the present invention are normally liquids at room temperature (about 20° to about 27° C.) and have the general formula $C_nH_n$, but can be substituted with one or more linear or branched $C_1$–$C_4$ alkyl groups; or other groups that do not interfere with the reaction. Toluene (n=6, methyl substituent) and xylene are particularly preferred aromatic hydrocarbons for use in the practice of the present invention.

The so-called dipolar aprotic solvent are well known as such in the art. Such solvents have a permanent dipole, but no readily removable hydrogen atoms. Examples of well-known dipolar aprotic solvents include dimethyl formamide (DMF), dimethyl acetamide (DMAC), dimethyl sulfoxide (DMSO), N-methylpyrrolidone (NMP) and the like. Dimethyl formamide is a preferred dipolar aprotic solvent for use in the practice of the present invention in its several embodiments.

The solvent used can also be a mixture of one or more of the same or different classes (types) of solvent described above.

Bases useful in the practice of the present invention include inorganic bases. Inorganic bases are inorganic compounds that are capable of reacting with and neutralizing an acid, especially a Brønstead acid. Examples of inorganic bases include alkali metal and alkaline earth metal oxides, hydroxides, bicarbonates, and carbonates. Alkali metal carbonates, especially sodium carbonate, are preferred inorganic bases for use in the practice of the present invention.

When an optional alkali metal halide is used, sodium iodide is the preferred alkali metal halide.

11-piperazinyl dibenzo[b,f]-[1,4]thiazepine hydrochloride, 2-(2-chloroethoxy)ethanol, solvent, base, preferably inorganic base, alkali metal halide, and phase transfer catalyst are combined, in any order, in a suitable reaction vessel that is preferably equipped with an agitator.

The relative molar amounts of the materials combined are not critical. Typically, the molar amount of chloroethoxy ethanol will be 1 to 2 times the molar amount of the thiazepine hydrochloride; the molar amount of base will be 4 to 8 times the molar amount of the thiazepine hydrochloride; and the amount of alkali metal iodide will be a fraction of the molar amount of thiazepine hydrochloride. The phase transfer catalyst is used in an amount of about 0.1% to about 0.7% on a weight basis. Typically, the reaction mixture will initially be about 0.5M to 1.5M in the thiazepine hydrochloride, but higher or lower concentrations can be used whilst realizing the benefits of the present invention.

The contents of the reaction vessel are preferably protected from excessive atmospheric water by providing a pad of dry inert gas over the reaction mixture, or by isolating the interior of the reaction vessel from the environment through a desiccant (e.g. molecular sieves, $CaCl_2$, or the like). The contents of the reaction vessel are heated to a reaction temperature of from about 80° C. to about 100° C. or higher, preferably to the reflux temperature. The reaction mixture is held at the reaction temperature for a reaction time of about 12 to about 24 hours. Typically, a reaction time of about 17 hours is sufficient. At the end of the reaction time, the reaction is a solid/liquid slurry.

The two-phase (s/l) reaction mixture is cooled and the solid phase separated by a suitable means whereby a liquid filtrate containing the product (quetiapine base) is obtained. The separation can be by any means known in the art, for example filtration (gravity or suction) or centrifugation—decanting, to mention just two.

The product quetiapine base can be isolated from the filtrate by any means known in the art, for example distillation/evaporation of the solvent, preferably at reduced pressure (<100 mm Hg).

Pharmaceutically acceptable acid addition salts are salts obtainable from quetiapine base by qutemarization of at least one amine functionality in the product; can be readily processed to the desired dosage form; and are nontoxic at the dosages used. The isolated quetiapine can be converted to a pharmaceutically acceptable acid addition salt by dissolving it in a salinization solvent and combining the solution so obtained with the desired acid, for example fumaric acid. Typically, the acid addition salt will precipitate from the salinization solvent upon cooling (if not before) and can be isolated by any means known in the art, for example filtration (gravity or suction) or centrifugation—decanting, to mention just two. Salinization solvents useful in the practice of the present invention include water, alcohols (e.g. methanol, ethanol, butanol), esters (e.g. ethyl or butyl acetate), ketones (e.g. acetone), DMF, DMSO, or mixtures of solvents like DMSO/chloroform, DMF/water, or NMP/acetonitrile.

In another and preferred embodiment, the quetiapine product is converted to a pharmaceutically acceptable acid addition salt, preferably the hemifumarate, without being isolated from the first filtrate. In this embodiment, first liquid filtrate is obtained as above and combined with the desired amount of acid, e.g. fumaric acid. The resulting combination is optionally heated to about 100° C. and thereafter cooled, whereby a second slurry, containing solid acid addition salt, is obtained. The pharmaceutically acceptable acid addition salt is isolated from the second slurry by any means known in the art, for example filtration (gravity or suction) or centrifugation—decanting, to mention just two. If desired, the pharmaceutically acceptable acid addition salt can be recrystallized using, for example, any of the salinization solvents mentioned above. In particular, the crude quetiapine hemifumarate can be advantageously recrystallized from a solvent that is a lower alkanol, preferably ethanol or isopropanol, mist preferably ethanol; or a mixture of water and a hereinabove described dipolar aprotic solvent, preferably dimethyl formamide.

Quetiapine or an acid addition salt thereof obtained by the process of the present invention can be formulated into pharmaceutical dosage forms suitable for oral or parenteral administration by methods known in the art.

The present invention is certain of its embodiments is illustrated by the following nonlimiting working and comparative examples.

EXAMPLE 1

Reagents:
 11-piperazinyl dibenzo[b,f]-[1,4]thiazepine hydrochloride 2.75 gr (7.5 mmole)
 2-(2-chloroethoxy)ethanol 1.2 gr (9.6 mmole)
 $Na_2CO_3$ 4.75 gr (45 mmole)
 NaI 40–50 mg (ca. 0.3 mmole)
 n-Butanol 15 mL
 TBAB 0.5 gr Procedure:
 The reagents were charged to a round-bottomed flask and heated to 115° C.–120° C. under gentle reflux conditions for 24 hours. The heating was discontinued and the solution was cooled. The resulting slurry was filtered. The precipitate was washed twice with small portions of butanol. The washing were combined with the filtrate and the precipitate discarded. Fumaric acid (0.435 g, 3.75 mmole) was added to the filtrate, the mixture was heated on a boiling water bath. The flask was removed from the bath and quetiapine hemifumarate crystallized out. The precipitae was collected (isolated) by filtration and recrystallized from 28 mL ethanol, yielding 2.0 grams (60.4%).

EXAMPLE 2

Reagents:
 11-piperazinyl dibenzo[b,f]-[1,4]thiazepine hydrochloride 5.5 gr (15 mmole)
 2-(2-Chloroethoxy)ethanol 2.4 gr (19 mmole)
 $Na_2CO_3$ 9.5 gr (90 mmole)
 NaI 90 mg (0.6 mmole)
 n-Butanol 30 mL
 TBAB 1 gr Procedure:
 The reagents were charged to a round-bottomed flask equipped with a magnetic stirrer and a condenser with a calcium chloride drying tube. The flask was set in an oil bath at 115° C.–120° C. and the contents of the flask stirred under gentle reflux. After 24 hours the heating was discontinued. The mixture was cooled and filtered. The precipitate collected on the Buchner filter was washed 2 times with butanol. The washings were combined with the filtrate and the precipitate was discarded. The filtrate was charged to a reaction vessel and fumaric acid (870 mg, 7.5 mmole) was charged to the vessel. The mixture was heated on an oil bath to boiling. The vessel was removed from the oil bath and the contents allowed to cool, whereupon quetiapine hemifumarate crystallized out. The product hemifumarate was filtered and recrystallized from 60 mL n-butanol.

Yield 4.7 grams (70.8%).

EXAMPLE 3

Reagents:
 11-piperazinyl dibenzo[b,f][1,4]thiazepine hydrochloride 16.5 gr (44 mmole)
 2-(2-Chloroethoxy)ethanol 7.2 gr (58 mmole)
 $Na_2CO_3$ 28.5 gr (270 mmole)
 NaI 270 mg (0.18 mmole)
 TBAB 3 gr
 Toluene 82.5 mL Procedure:
 The reagents were charged to a round-bottomed flask equipped with a magnetic stirrer and a condenser with a calcium chloride drying tube. The flask and contents were heated in an oil bath at 105° C. under gentle reflux. After 24 hours, a Dean Stark trap was attached to the flask and the azeotropic mixture of water and toluene was distilled out. The product remaining in the flask was filtered-off. The precipitate (salts) was washed on the Buchner filter with small portions of toluene. The washings were combined with the filtrate and the precipitate was discarded.
 To the filtrate contained in a flask was added 2.6 gr (22 mmole) fumaric acid. The mixture was heated to boiling on a heating bath and then was removed from the heating bath and stirring of the contents of the flask was continued. The quetiapine hemifumarate crystallized out. The flask was cooled in an ice bath and the contents filtered. The collected solid was recrystallized from 150 mL ethanol. Yield 14.0 grams 72%.

EXAMPLE 4

Reagents:
 11-piperazinyl dibenzo[b,f][1,4]thiazepine hydrochloride 33 gr (86.9 mmole)
 2-(2-Chloroethoxy)ethanol 14.4 gr (115.6 mmole)
 $Na_2CO_3$ 57 gr
 NaI 540 mg
 TBAB 6 gr
 Toluene 165 gr Procedure:
 The reagents were charged to a round-bottomed flask equipped with a magnetic stirrer and a condenser with a calcium chloride drying tube. The flask was heated on an oil bath at 107° C. under gentle reflux.
 After 40 hours, the flask and contents were cooled slightly and contents of the flask filtered. The collected precipitate was washed with small portions of toluene. The washings were combined with the filtrate and the precipitate was discarded. The filtrate was divided into 4 equal portions, which were worked up in four different ways:

A:
 The filtrate was extracted with water. To the organic phase was added 1.43 gr (11.5 mmole) fumaric acid. The mixture was heated in a boiling water bath, removed from the bath and continued to stir. Quetiapine hemifumarate crystallized out. The product was filtered and recrystallized from 80 mL ethanol. Yield 6.91 grams 72%.

B:
 The filtrate was extracted with water. The organic phase was evaporated down to a small volume to which was added 1.43 gr (11.5 mmole) fumaric acid with 120 mL ethanol. The reactants were heated to boiling. The heating was stopped and the Quetiapine hemifumarate crystallized out. The product were continued to stir, filtered and recrystallized from 70 mL ethanol. Yield 6.36 grams (65.5%)

C:
 To the filtrate was added 1.43 gr (11.5 mmole) fumaric acid. It was heated in a boiling water bath, removed from the bath and let to stir. The Quetiapine hemifumarate crystallized out. The product was filtered and recrystallized from 90 mL ethanol. Yield 7.12 grams (73.3%).

D:
 The filtrate was concentrated down to a small volume. 1.433 gr (11.5 mmole) fumaric acid was added with 120 mL ethanol. The mixture was heated to boiling, and removed from the heating bath. The Quetiapine hemifumarate crystallized out and was cooled, filtered and recrystallized from 70 mL ethanol. Yield 6.62 grams (68.1).

EXAMPLE 5

Comparative

Reagents:
 11-piperazinyl dibenzo{b,f][1,4]thiazepinehydrochloride 2.75 gr (7.5 mmole)
 2-(2-Chloroethoxy)ethanol 1.2 gr (9.6 mmole)
 $Na_2CO_3$ 4.75 gr NaI 40–50 mg
Toluene 15 mL Procedure:

The reagents were charged to a round-bottomed flask equipped with a magnetic stirrer and a condenser with a calcium chloride drying tube. The flask and contents were heated in an oil bath at 115° C.–120° C. under gentle reflux.

The progress of the reaction was checked by HPLC after 17 hours and the contents of the flask contained 91.6% product and 7.1% starting material.

EXAMPLE 6

Reagents:

11-piperazinyl dibenzo{b,f][1,4]thiazepinehydrochloride 2.75 gr (7.5 mmole)
2-(2-Chloroethoxy)ethanol 1.2 gr (9.6 mmole)
$Na_2CO_3$ 4.75 gr
NaI 40–50 mg
Toluene 15 mL
TBAB 0.5 grams Procedure:

The reagents were charged to a round-bottomed flask equipped with a magnetic stirrer and a condenser with a calcium chloride drying tube. The flask and contents were heated on an oil bath at 115° C.–120° C. under gentle reflux.

After 17 hours the progress of the reaction was checked by HPLC analysis of the contents of the flask which were found to include 98.2% product and 0.45% starting material.

EXAMPLE 7

Comparative

Reagents:

11-piperazinyl dibenzo[b,f]-[1,4]thiazepine hydrochloride 2.75 gr (7.5 mmole)
2-(2-Chloroethoxy)ethanol 1.2 gr (9.6 mmole)
$Na_2CO_3$ 4.75 gr
NaI 40–50 mg
n-Butanol 15 mL Procedure:

The reactants were charged to a round-bottomed flask equipped with a magnetic stirrer and a condenser with a calcium chloride drying tube. The flask and contents heated in an oil bath at 115° C.–120° C. under gentle reflux.

After 17 hours, HPLC analysis showed the contents of the flask to include 94.1% product and 4.3% starting material.

EXAMPLE 8

Reagents:

11-piperazinyl dibenzo[b,f]-[1,4]thiazepine hydrochloride 2.75 gr (7.5 mmole)
2-(2-Chloroethoxy)ethanol 1.2 gr (9.6 mmole)
$Na_2CO_3$ 4.75 gr
NaI 40–50 mg
n-Butanol 15 mL
TBAB 0.5 gr Procedure:

The reagents were charged to a round-bottomed flask equipped with a magnetic stirrer and a condenser with a calcium chloride drying tube. The flask and contents were heated on an oil bath at 115° C.–120° C. with gentle reflux of the contents of the flask.

After 17 hours, HPLC analysis of the contents of the flask showed 96.9% product and 0.79% starting material.

EXAMPLE 9

Comparative

Reagents:

11-piperazinyl dibenzo[b,f]-[1,4]thiazepine hydrochloride 2.75 gr (7.5 mmole)
2-(2-Chloroethoxy)ethanol 1.2 gr (9.6 mmole)
$Na_2CO_3$ 4.75 gr
NaI 40–50 mg
DMF 10 mL Procedure:

The reagents were charged to a round-bottomed flask equipped with a magnetic stirrer and a condenser with a calcium chloride drying tube. The flask and contents were heated in an oil bath at 103° C. After 4 hours, HPLC analysis of the contents of the flask showed 73.8% product and 25.6% starting material. After 18 hours, HPLC analysis showed 95.4% product and 1.1% starting material.

EXAMPLE 10

Reagents:

11-piperazinyl dibenzo[b,f][1,4]thiazepinehydrochloride 2.75 gr (7.5 mmole)
2-(2-Chloroethoxy)ethanol 1.2 gr (9.6 mmole)
$Na_2CO_3$ 4.75 gr
NaI 40–50 mg
DMF 10 mL
TBAB 0.5 gr.

Procedure:

The reagents were charged to a round-bottomed flask equipped with a magnetic stirrer and a condenser with a calcium chloride drying tube. The flask and contents were heated in an oil bath at 103° C.

After 4 hours, HPLC analysis of the contents of the flask showed 89.7% product and 9.7% starting material. After 18 hours, HPLC analysis showed 95.5% product and 0.26% starting material.

EXAMPLE 11

A. Preparation of Crude OTP Hemifumarate

A 100 liter reactor equipped with mechanical stirrer, condenser, and thermometer, was charged with n-BuOH (40.5 L), 11-piperazinyl dibenzo[b,f][1,4]thiazepinehydrochloride (15 kg), $Na_2CO_3$ (7.5 kg), TBAB (1.5 kg) and 2-(2-chloroethoxy)ethanol (5.25 L). The mixture was heated to 115° C. during which time a portion of the n-BuOH and water distilled out. The distillation was continued until all of the theoretical amount of water was distilled out and the vapor temperature dropped. The reaction mixture was stirred at a rate of 120 rpm. The temperature was maintained for 26.5 hours until completion of the reaction. The reaction mixture was cooled to 25° C. during 3 hours. The mixture was filtered on a filter press. The filtrate was filtered into another 160 liter reactor (5μ and 1μ filters), equipped with mechanical stirrer, condenser, and thermometer. To the filtrate, 2.24 kg of fumaric acid was added. The resulting mixture was heated to 100° C. over 2 hours and then cooled to 5° C. over 2 hours. The mixture was maintained at this temperature, with stirring, for an additional one hour. The resulting slurry was separated on a centrifuge and washed with n-BuOH (30L) and ethanol absolute (30L) to obtain 16.7 kg of wet, crude quetiapine fumarate.

B. Recrystallization of Crude OTP Hemifumarate From Ethanol.

A 100 liter reactor equipped with mechanical stirrer, condenser, and thermometer, was charged with the wet material obtained as above (5.9 kg) and with ethanol absolute (80 L). The mixture was then heated to reflux (80° C.) and stirred at a rate of 120 rpm. The heating was continued for 2 hours. A clear solution was obtained. The clear solution was filtered through a-5,1,0,2-micron filer. The filtrate was then transferred to a preheated 160 liter reactor equipped with mechanical stirrer, condenser, and thermometer. The clear solution was reheated to reflux (80° C.) and stirred at a rate of 120 rpm. The heating was continued for 1 hour until a clear solution was obtained. The clear solution was cooled to 10° C. during 12 hours and maintained at this temperature for another 5 hours. The resulting slurry was separated on a centrifuge and washed with ethanol absolute (10L) to obtain 4.3 kg of wet quetiapine fumarate cryst.

A portion of the wet material was pecked into a stirred drier and dried at 65° C., 60 mmHg at a rate of 12 rpm for 5 hours.

What is claimed is:

1. A process for making quetiapine comprising the step of reacting 11-piperazinyl dibenzo[b,f]-[1,4]thiazepine hydrochloride and 2-(2-chloroethoxy) ethanol in a solvent in the presence of a base, and a phase transfer catalyst.

2. The process of claim 1 wherein the reacting is at reflux temperature.

3. The process of claim 1 wherein the reacting is performed in the presence of an alkali metal halide.

4. The process of claim 3 wherein said alkali metal halide is sodium iodide.

5. The process of claim 1 wherein the phase transfer catalyst is selected from the group consisting of tetrabutylammonium bromide, triethylbenzylammonium chloride, tricaprylmethylammonium chloride and tetrabutylammonium hydroxide.

6. The process of claim 5 wherein the phase transfer catalyst is tetrabutylammonium bromide.

7. The process of claim 1 wherein the solvent is a lower alkanol, an aromatic hydrocarbon, or dipolar aprotic solvent, or a mixture of one or more of these.

8. The process of claim 7 wherein the solvent is n-butanol.

9. The process of claim 7 wherein the solvent is toluene.

10. The process of claim 7 wherein the solvent is dimethyl formamide.

11. The process of claim 1 wherein the base is selected from the group consisting of an alkali metal and alkaline earth metal oxides, hydroxides, bicarbonates and carbonates.

12. The process of claim 11, wherein said base is sodium carbonate.

13. A process for making quetiapine hemifumarate comprising the steps of:
a) reacting 11-piperazinyl dibenzo[b,f]-[1,4]thiazeine hydrochloride and 2-(2-chloroethoxy)ethanol in a solvent in the presence of a base, and a phase transfer catalyst, whereby a first slurry is obtained,
b) separating the solid from the first slurry whereby a liquid filtrate is obtained,
c) combining the liquid filtrate with fumaric acid, whereby a second slurry is obtained, and
d) isolating quetiapine hemifumarate from the second slurry.

14. The process of claim 13 wherein the combination of step c) is heated to a temperature of about 80° C. to about 100° C. or higher and subsequently cooled to a temperature less than about 100° C., whereby a slurry is obtained.

15. The process of claim 13 wherein the reacting is at a temperature of about 100° C.

16. The process of claim 13 wherein the reacting is performed in the presence of an alkali metal halide.

17. The process of claim 16 wherein said alkali metal halide is sodium iodide.

18. The process of claim 13 wherein the phase transfer catalyst is selected from the group consisting of tetrabutylammonium bromide, triethylbenzylammonium chloride, tricaprylmethylammonium chloride, and tetrabutylammonium hydroxide.

19. The process of claim 18 wherein the phase transfer catalyst is tetrabutylammonium bromide.

20. The process of claim 13 wherein the solvent is a lower alkanol, an aromatic hydrocarbon, or dipolar aprotic solvent, or a mixture of one or more of these.

21. The process of claim 20 wherein the solvent is n-butanol.

22. The process of claim 20 wherein the solvent is toluene.

23. The process of claim 20 wherein the solvent is dimethyl formamide.

24. The process of claim 13 wherein the base is selected from the group consisting of an alkali metal and alkaline earth metal oxides, hydroxides, bicarbonates and carbonates.

25. The process of claim 24 wherein the base is sodium carbonate.

26. The process of claim 13 further comprising the step of recrystallizing the isolated quetiapine hemifumarate from a solvent selected from the lower alkanols and mixtures of a dipolar aprotic solvent and water.

27. The process of claim 26 wherein the lower alkanol is ethanol or isopropanol and the dipolar aprotic solvent is dimethyl formamide.

28. In a process for making quetiapine or a pharmaceutically acceptable salt thereof, the step of reacting 11-piperazinyl dibenzo[b,f]-[1,4]thiazepine hydrochloride and 2-(2-chloroethoxy)ethanol in a solvent that is a lower alkanol, an aromatic hydrocarbon, or a dipolar aprotic solvent, in the presence of sodium carbonate, sodium iodide, and tetrabutylammonium bromide.

29. The process of claim 28 wherein the pharmaceutically acceptable salt is the hemifumarate.

30. A process for making quetiapine comprising the step of reacting, at reflux, 11-piperazinyl dibenzo [b,f]-[1,4] thiazepine hydrochloride and 2-(2-chloroethoxy)ethanol in a solvent selected from n-butanol, toluene, and dimethyl formamide, in the presence of sodium carbonate, sodium iodide, and tetrabutylammonium bromide.

31. A process for making quetiapine hemifumarate comprising the steps of:
a) reacting, at reflux, 11-piperazinyl dibenzo[b,f]-[1,4] thiazapine hydrochloride and 2-(2-chloroethoxy)ethanol in a solvent selected from n-butanol, toluene, and dimethyl formamide in the presence of sodium carbonate, and tetrabutyl ammonium bromide, whereby a first slurry is obtained,
b) separating the solid from the first slurry whereby a liquid filtrate is obtained, c) combining the liquid filtrate with fumaric acid,
d) heating the combination to a temperature of about 100° C. or higher,
e) subsequently cooling the combination to <100° C., whereby a second slurry is obtained, and
f) isolating quetiapine hemifumarate from the second slurry.

32. The process of claim 31 wherein the reacting is carried-out also in the presence of sodium iodide.

33. The process of claim 31 further comprising the step of recrystallizing the quetiapine hemifumarate isolated in step f) from a solvent selected from the lower alkanol or a mixture of a dipolar aprotic solvent and water.

34. The process of claim 33 wherein the lower alkanol is ethanol or isopropanol and the dipolar aprotic solvent is dimethyl formamide.

* * * * *

UNITED STATES PATENT AND TRADEMARK OFFICE
CERTIFICATE OF CORRECTION

| | | |
|---|---|---|
| PATENT NO. | : 7,071,331 B2 | Page 1 of 2 |
| APPLICATION NO. | : 10/785244 | |
| DATED | : February 23, 2004 | |
| INVENTOR(S) | : Dov Diller et al. | |

It is certified that error appears in the above-identified patent and that said Letters Patent is hereby corrected as shown below:

Column 1, lines 18-19, change "2-(2-(4-dibenzo[b,f]-[l,4]thiazepin-11-yl-l-piperazinyl)ethoxy)ethanol" to -- 2-(2-(4-dibenzo[b,f]-[l,4]thiazepine-11-yl-l-piperazinyl)ethoxy)ethanol --

Column 2, lines 7-8, change "...tetrabutyammonium bromide..." to -- tetrabutylammonium bromide --

Column 2, line 14, change "...recrystallizion..." to -- recrystallization --

Column 2, lines 41-42, change "...the well-know dihydrochloride..." to -- the well-known dihydrochloride --

Column 2, line 55, change "...in the practice opf the present invention..." to -- in the practice of the present invention --

Column 4, line 8, change "...obtainable from quetiapine base by qutemarization..." to -- obtainable from quetiapine base by quaternization --

Column 4, line 49, change "The present invention is certain of its embodiments..." to -- The present invention in certain of its embodiments --

Column 5, line 7, change "The precipitae was collected..." to -- The precipitate was collected --

Column 6, line 64, change "11-piperazinyl dibenzo{b,f][1,4] thiazepinehydrochloride" to -- 11-piperazinyl dibenzo[b,f][1,4] thiazepine hydrochloride --

Column 7, line 16, change "11-piperazinyl dibenzo{b,f][1,4] thiazepinehydrochloride" to -- 11-piperazinyl dibenzo[b,f][1,4] thiazepine hydrochloride --

UNITED STATES PATENT AND TRADEMARK OFFICE
CERTIFICATE OF CORRECTION

PATENT NO. : 7,071,331 B2
APPLICATION NO. : 10/785244
DATED : February 23, 2004
INVENTOR(S) : Dov Diller et al.

It is certified that error appears in the above-identified patent and that said Letters Patent is hereby corrected as shown below:

Column 9, line 9, change "...Recrystallization of Crude OTP Hemifumarate..." to -- Recrystallization of Crude QTP Hemifumarate --

Column 9, line 17, change "a-5,1,0,2-micron filer" to -- a-5,1,0.2-micron filter --

Column 9, line 62, change "11-piperazinyl dibenzo[*b,f*]-[1,4]thiazeine" to -- 11-piperazinyl dibenzo[*b,f*]-[1,4]thiazepine --

Column 10, lines 60-61, change "11-piperazinyl dibenzo[*b,f*]-[1,4]thiazapine" to -- 11-piperazinyl dibenzo[*b,f*]-[1,4]thiazepine --

Signed and Sealed this

Seventh Day of July, 2009

JOHN DOLL
*Acting Director of the United States Patent and Trademark Office*